United States Patent
Lin et al.

(10) Patent No.: US 11,925,701 B2
(45) Date of Patent: Mar. 12, 2024

(54) METHOD FOR SKIN CONDITIONING BY USING DAN FENG PEONY EXTRACT

(71) Applicant: TCI CO., LTD., Taipei (TW)

(72) Inventors: Yung-Hsiang Lin, Taipei (TW);
Wei-Chun Lee, Taipei (TW)

(73) Assignee: TCI CO., LTD., Taipei (TW)

( * ) Notice: Subject to any disclaimer, the term of this patent is extended or adjusted under 35 U.S.C. 154(b) by 57 days.

(21) Appl. No.: 17/510,412

(22) Filed: Oct. 26, 2021

(65) Prior Publication Data
US 2022/0125708 A1   Apr. 28, 2022

Related U.S. Application Data

(60) Provisional application No. 63/105,909, filed on Oct. 27, 2020.

(51) Int. Cl.
*A61K 8/9789* (2017.01)
*A61Q 19/00* (2006.01)

(52) U.S. Cl.
CPC .......... *A61K 8/9789* (2017.08); *A61Q 19/007* (2013.01); *A61K 2800/92* (2013.01)

(58) Field of Classification Search
None
See application file for complete search history.

(56) References Cited

FOREIGN PATENT DOCUMENTS

| | | | |
|---|---|---|---|
| CN | 1984637 A | | 6/2007 |
| CN | 101111244 B | | 4/2011 |
| CN | 103564112 A | * | 2/2014 |
| JP | 2012087112 A | * | 5/2012 |
| KR | 20130083796 A | | 7/2013 |
| KR | 101901451 B1 | * | 9/2018 |
| KR | 20190013121 A | | 2/2019 |

OTHER PUBLICATIONS

Analysis of Chemical Composition of Essential Oil from Feng Dan Peony, Huipan Yu et al., Zhangqiaokeyan, 2014 Abstract.
Chemical Constituents From the Flower Petals of Paeonia suffruticosa Andr., Hui-Jiao Yan et al., Natural Product Research and Development vol. 27, 2015 Abstract.
Hydrolyzable Tannins as Antioxidants in the Leaf Extract of Eucalyptus globulus Possessing Tyrosinase and Hyaluronidase Inhibitory Activities, Keiichiro Sugimoto et al., Food Science and Technology Research vol. 15, 2009, pp. 331-336 Compound 11 on p. 333, Table 2.
To study the Flavonoids Constituents of the flowers of *Paeonia suffruticosa*., Wei Zhao et al.,Modem Chinese Medicine vol. 3, 2016 Abstract.
Topical Apigenin Improves Epidermal Permeability Barrier Homeostasis in Normal Murine Skin by Divergent Mechanisms, Maihua Hou et al., Exp Dermatol. Mar. 2013 Abstract, Results, Discussion, Fig 2.

* cited by examiner

*Primary Examiner* — Susan Hoffman
(74) *Attorney, Agent, or Firm* — Chieh-Mei Wang

(57) ABSTRACT

Provided is a method for skin conditioning comprising administering to a subject in need thereof a composition comprising a Dan Feng peony extract, where the Dan Feng peony extract is extracted from flowers of Dan Feng peony. The Dan Feng peony extract is used to increase the production of hyaluronic acid, maintain the structure of skin keratinocytes, and regulate the moisture content of skin cells.

12 Claims, 11 Drawing Sheets
Specification includes a Sequence Listing.

METHOD FOR SKIN CONDITIONING BY USING DAN FENG PEONY EXTRACT

CROSS-REFERENCE TO RELATED APPLICATION

This application claims the benefit of U.S. provisional application Ser. No. 63/105,909, filed on Oct. 27, 2020. The entirety of the above-mentioned patent application is hereby incorporated by reference herein and made a part of the specification.

REFERENCE OF AN ELECTRONIC SEQUENCE LISTING

The contents of the electronic sequence listing (P201300USI_ST25.txt; Size: 4.18KB; and Date of Creation: Dec. 29, 2021) is herein incorporated by reference in its entirety.

BACKGROUND

Technical Field

The present invention relates to a Dan Feng peony extract, and in particular, to use of a Dan Feng peony extract for preparing a skin conditioning composition.

Related Art

The peony is a deciduous shrub in the genus *Paeonia*, the family Paeoniaceae. Its beautiful flowers are of ornamental value. The peony grows in the Shandong, Henan, Shaanxi, and Anhui provinces of China.

The Great Dictionary of Traditional Chinese Medicine clearly states that: "the quality of the root bark of the peony tree from the Fenghuang mountain in Tongling, Anhui is the best", so that it is referred to as Feng Dan or Dan Feng. The dried root bark of Dan Feng has the effects of clearing heat from blood, promoting blood circulation, and removing blood stasis.

SUMMARY

To enhance the value of peony, the inventor continues to research and develop peony flower-related products and their uses.

In view of this, the present invention provides use of a Dan Feng peony extract for preparing a skin conditioning composition, where the Dan Feng peony extract is extracted from flowers of Dan Feng peony.

In an embodiment, the Dan Feng peony extract is used to increase the production of hyaluronic acid in skin cells.

In an embodiment, the Dan Feng peony extract is used to increase the expression level of HAS2 gene and HAS3 gene.

In an embodiment, the Dan Feng peony extract is used to enhance skin moisturizing fibers. In an embodiment, the Dan Feng peony extract is used to maintain the structure of skin keratinocytes.

In an embodiment, the Dan Feng peony extract is used to increase the expression level of Tgm1 gene and keratin-related gene.

In an embodiment, the Dan Feng peony extract is used to regulate the moisture content of skin cells. In an embodiment, the Dan Feng peony extract is used to increase the expression level of AQP3 gene and GBA gene.

In an embodiment, the Dan Feng peony extract is used to increase the content of skin filaggrin. In an embodiment, the Dan Feng peony extract is used to increase the expression level of FLG gene. The increase of the expression level of FLG gene can increase the content of skin filaggrin and further increase the content of natural moisturizing factors (NMFs). Herein, the NMF is a complex mixture of water-soluble substances with a low relative molecular mass, and various components of the NMF are produced by the filaggrin through a series of processes.

In an embodiment, the skin conditioning refers to increasing skin hydration, reducing trans-epidermal water loss (TEWL), improving skin elasticity, and the like.

In an embodiment, the skin conditioning composition is a food composition, and the effective dose of the Dan Feng peony extract is 4 mL/day.

In an embodiment, the skin conditioning composition is a topical composition, and the effective concentration of the Dan Feng peony extract is at least 5%.

Based on the above, the Dan Feng peony extract according to any embodiment of the present invention can be used for preparing the skin conditioning composition. In other words, the foregoing composition has one or more of the following functions: increasing the production of hyaluronic acid in skin cells, increasing the content of skin moisturizing fibers, maintaining the structure of skin keratinocytes, increasing the content of skin filaggrin, regulating the moisture content of skin cells, reducing TEWL, improving skin elasticity, and the like.

DETAILED DESCRIPTION

Figure 1:
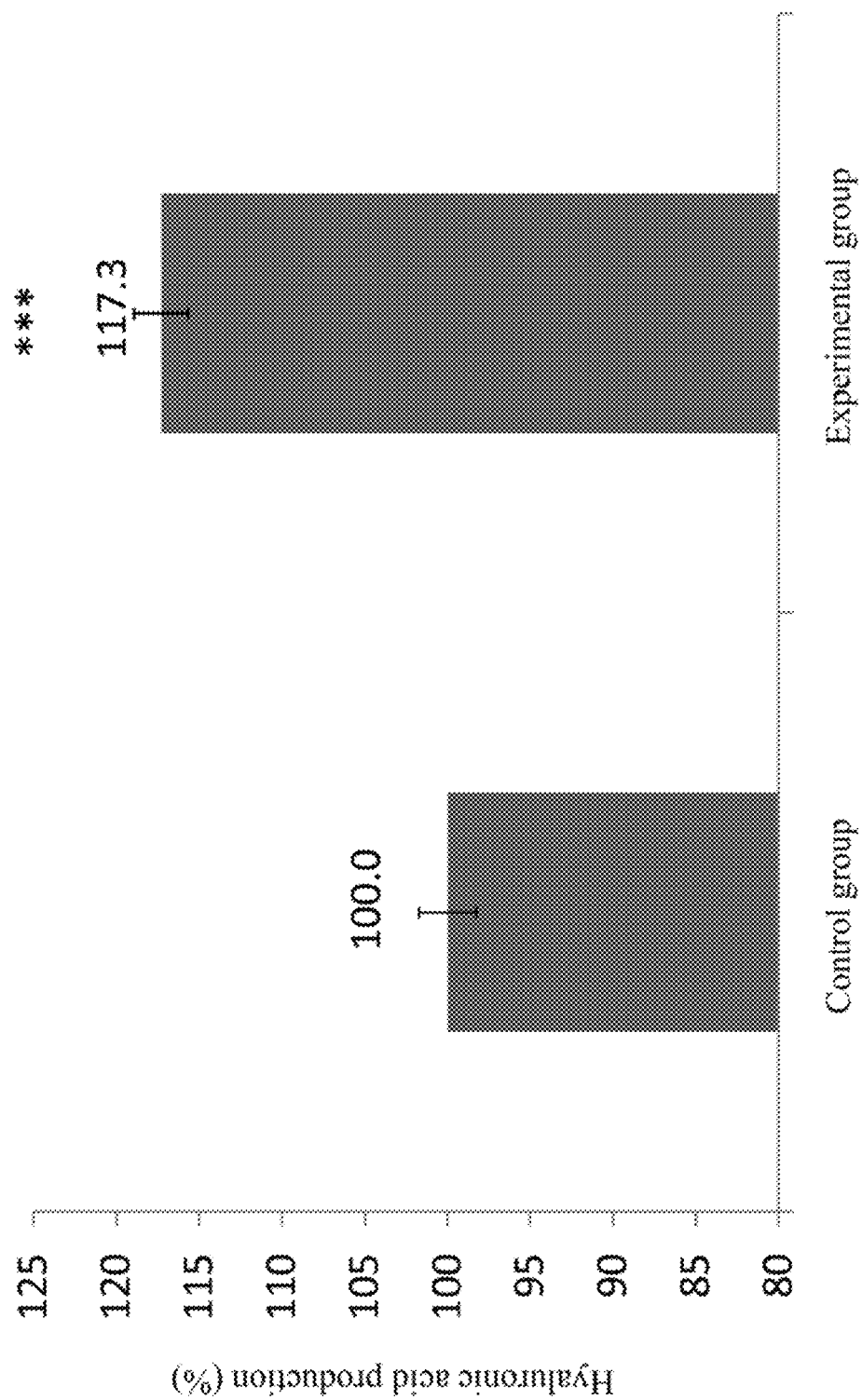
FIG. 1 is a graph showing an experimental result of a Dan Feng peony extract promoting the production of hyaluronic acid.

As used herein, a concentration symbol "%" generally refers to weight percent concentration, and a concentration symbol "vol %" generally refers to volume percent concentration.

As used herein, "Dan Feng peony" generally refers to flowers of the Dan Feng peony. The flowers may be original, dried, or processed by other physical methods to facilitate processing, and may further be whole, chopped, diced, milled, ground, or processed by other methods to affect the size and physical integrity of the original material.

In some embodiments, a Dan Feng peony extract refers to a product prepared by extracting, filtering, concentrating, sterilizing and drying the flowers of Dan Feng peony. For example, after the Dan Feng peony flowers are washed, extraction is carried out with an extracting solvent to obtain a preliminary extracted liquid, the preliminary extracted liquid is then filtered to remove impurities, and the filtered preliminary extracted liquid is then concentrated to obtain a concentrated liquid. Herein, the concentrated liquid is the Dan Feng peony extract.

In some embodiments, the Dan Feng peony flowers are first picked manually or by machine and then washed with water for use. The flowers and the extracting solvent of water, alcohol, or alcohol-water mixture, preferably water, are mixed in a weight ratio of 15-75:1-5, and then subjected to extraction in the solvent at 50-100° C. for 0.5-3 h after homogenization. The mixture is cooled to room temperature after the extraction, and a preliminary extracted liquid is filtered with a 400 mesh filter to obtain a filtrate. The filtrate is concentrated under reduced pressure at 45-70° C. to obtain a concentrated liquid. Finally, the concentrated liquid is spray dried by using a spray drying machine to obtain a powder, which is a Dan Feng peony extract of an embodiment of the present invention.

In some other embodiments, the foregoing concentrated liquid is then sterilized, and the sterilized concentrated liquid is then dried by spray drying into a powder. Herein, the dried powder is a Dan Feng peony extract of another embodiment of the present invention.

In some embodiments, a Dan Feng peony extract may be a commercially available Dan Feng peony extracted liquid or Dan Feng peony extracted powder. In some embodiments, a Dan Feng peony extract is 1 kg of extract obtained from 10 kg of flower raw materials.

In an embodiment, a Dan Feng peony extract is in powder form. In an embodiment, a Dan Feng peony extract is an edible powder.

In an embodiment, the present invention provides use of a Dan Feng peony extract for preparing a skin conditioning composition, where the Dan Feng peony extract is extracted from flowers of Dan Feng peony.

In an embodiment, the Dan Feng peony extract is used to increase the production of hyaluronic acid in skin cells. Hyaluronic acid can prevent natural aging of the skin, and protect the skin from the damage caused by the sun's ultraviolet rays, tobacco smoke, and air pollutants. Hyaluronic acid can also help increase skin moisture, so that the skin structure is firm and plump, so as to reduce skin fine texture and wrinkles. In addition, hyaluronic acid also plays a key role in wound healing. When skin cells need to be repaired or are damaged, the concentration of hyaluronic acid will also increase, and its use on skin wounds has been proven to reduce the size of the wound and relieve pain. It can also help reduce the risk of wound cell infection. Moreover, hyaluronic acid is also helpful for osteoarthritis. It is shown from experiments that consuming hyaluronic acid every day for at least two months can significantly relieve the knee joint pain in patients with osteoarthritis. Hyaluronic acid can also help relieve gastric acid reflux symptoms. Hyaluronic acid has excellent moisturizing properties, so that it is also commonly used to treat dry eye syndrome, slow down osteoporosis, relieve bladder pain syndrome, and the like.

In an embodiment, the Dan Feng peony extract is used to increase the expression level of HAS2 gene and HAS3 gene. Increased HAS2 gene expression level can promote skin cells to produce high-molecular hyaluronic acid. The high-molecular hyaluronic acid has viscosity and support properties, which can support the structure of the skin and improve skin sagging. Increased HAS3 gene expression level can promote skin cells to synthesize small-molecular hyaluronic acid. The small-molecular hyaluronic acid has water retention properties, which can maintain the water retention of the skin and improve skin wrinkles and fine texture.

In an embodiment, the Dan Feng peony extract is used to enhance skin moisturizing fibers. In an embodiment, the Dan Feng peony extract is used to maintain the structure of skin keratinocytes.

In some embodiments, the Dan Feng peony extract is used to increase the expression level of Tgm1 gene and keratin-related gene. Increased Tgm1 gene expression level can maintain the skin keratinocyte membrane, so that water loss can be prevented in the stratum corneum. Increased keratin-related gene expression level can maintain the structure of keratinocytes to be tight and integral, so that the stratum corneum can protect the inner layer of the skin soft and tender. Herein, the keratin-related gene includes the KRT1 gene, KRT10 gene, and KRT14 gene.

In an embodiment, the Dan Feng peony extract is used to regulate the moisture content of skin cells. In an embodiment, the Dan Feng peony extract is used to increase the expression level of AQP3 gene and GBA gene. Increased AQP3 gene expression level can increase the content of aquaporin in the skin. The aquaporin is a transport protein that transports small molecules such as water, glycerol, and urea across cell membranes. In addition, the AQP3 gene is involved in skin hydration, skin barrier function, and wound healing, which can maintain the normal shape and function of the skin. Increased GBA gene expression level indicates an increase in ceramide synthase. The ceramide is a lipid in the interstitial skin keratinocytes and is a moisturizing ingredient.

In an embodiment, the Dan Feng peony extract is used to enhance skin moisturizing fibers. In an embodiment, the Dan Feng peony extract is used to increase the expression level of FLG gene. Increased FLG gene expression level can increase the content of filaggrin in the skin. The filaggrin is used to connect keratin fibers for regular aggregation of the keratin fibers, so as to form a physical barrier on the outermost layer of the skin. The most important pathogenic gene for atopic dermatitis is the mutation of filaggrin. Abnormal filaggrin leads to the loss of stratum corneum function and greatly reduced skin moisturizing degree, further resulting in dry skin and dermatitis.

In an embodiment, the skin conditioning refers to increasing skin hydration, reducing trans-epidermal water loss (TEWL), improving skin elasticity, and the like.

In an embodiment, the skin conditioning composition is a food, drink, or nutritional supplement, and the effective dose of the Dan Feng peony extract is 4 mL/day. In other words, the food, drink, or nutritional supplement contains a specific content of the Dan Feng peony extract. In some embodiments, the food may be a general food, food for special health use (FoSHU), dietary supplement, or food additive.

The FoSHU may also be referred to as functional food, which refers to high-functional food that is processed to provide nourishment and effectively express the body regulating function. Herein, the "functional" refers to regulating nutrients for the structure and function of the human body or obtaining useful effects for health care purposes such as physiological effects. The food of the present invention may be prepared by methods commonly used in the art. The food may be prepared by adding raw materials and ingredients commonly added in the art. In addition, the dosage form of the food can be prepared without limitation as long as it is regarded as a dosage form of a food. The composition for food of the present invention may be prepared in various dosage forms. Different from general medicines, the food is used as the raw material, so that there are no side effects that may occur due to long-term use of medicines. The excellent portability allows the food of the present invention to be ingested as an auxiliary agent for enhancing the immune-enhancing effect.

In some embodiments, the foregoing food may be manufactured into a dosage form suitable for oral administration using techniques well known to those skilled in the art. In some embodiments, general foods may be, but are not limited to: beverages, fermented foods, bakery products, or condiments.

The foregoing composition may further include a physiologically acceptable carrier, types of the carrier are not particularly limited, and any carrier commonly used in the technical field may be used.

In addition, the composition may contain additional ingredients that are commonly used in foods to improve smell, taste, vision, and the like. For example, the composition may contain 0.1-5 wt % of vitamins A, C, D, E, B1, B2, B6, B12, niacin, biotin, folate, panthotenic acid, etc. In addition, the composition may contain minerals such as Zn, Fe, Ca, Cr, Mg, Mn, and Cu. In addition, the composition may contain amino acids such as lysine, tryptophan, cysteine, and valine.

In addition, the composition may contain food additives such as antioxidants (such as butylated hydroxyanisole (BHA) and butylated hydroxytoluene (BHT)), colorants (such as tar pigment), fragrances (such as vanillin and lactone), color coupler (such as sodium nitrite), preservatives (such as potassium sorbate, sodium benzoate, salicylic acid, and sodium dehydroacetate), bleach (such as sodium sulfite), condiments (such as monosodium glutamate), sweeteners (such as dulcin, cyclamate, saccharin, and sodium), expanding agents (such as potassium alum and D-potassium hydrogen tartrate), fortifiers, emulsifiers, thickeners (such as thickening agents), coating agents, gum base agents, foam inhibitors, solvents, and improvers. One or more of the foregoing additives may be selected to be added in a proper amount according to food types.

In some embodiments, the Dan Feng peony extract (as a food additive) of any embodiment can be added during the preparation of raw materials by conventional methods, or the Dan Feng peony extract (as a food additive) of any embodiment is added in the food preparation process to be prepared with any edible material into an edible product for humans and non-human animals to eat.

In some embodiments, the foregoing composition may be a medicament. In other words, the medicament contains the Dan Feng peony extract with an effective content.

In some embodiments, the foregoing medicament may be manufactured into a dosage form suitable for enteral or oral administration using techniques well known to those skilled in the art. The dosage form includes, but is not limited to: a tablet, a troche, a lozenge, a pill, a capsule, a dispersible powder or granule, a solution, a suspension, an emulsion, a syrup, an elixir, a slurry, and other similar substances.

In some embodiments, the foregoing medicament may be manufactured into a dosage form suitable for parenteral or topical administration using techniques well known to those skilled in the art. The dosage form includes, but is not limited to: an injection, a sterile powder, an external preparation, and other similar substances. In some embodiments, the medicament may be administered by a parenteral route selected from a group consisting of the following: subcutaneous injection, intraepidermal injection, intradermal injection, and intralesional injection.

In some embodiments, the medicament may further include a pharmaceutically acceptable carrier widely used in drug manufacturing technology. For example, the pharmaceutically acceptable carrier may include one or more of the following reagents: a solvent, a buffer, an emulsifier, a suspending agent, a decomposer, a disintegrating agent, a dispersing agent, a binding agent, an excipient, a stabilizing agent, a chelating agent, a diluent, a gelling agent, a preservative, a wetting agent, a lubricant, an absorption delaying agent, a liposome, and other similar substances. The selection and quantity of these reagents fall within the scope of professionalism and routine technology of those skilled in the art.

In some embodiments, the pharmaceutically acceptable carrier includes a solvent selected from a group consisting of the following: water, normal saline, phosphate buffered saline (PBS), and aqueous solution containing alcohol.

In an embodiment, the skin conditioning composition is a topical composition, and the effective concentration of the Dan Feng peony extract is at least 5%. In some embodiments, the topical composition may be a cosmetic or a cosmeceutical. In other words, the cosmetic or the cosmeceutical contains a specific content of the Dan Feng peony extract.

In some embodiments, the cosmetic or the cosmeceutical may be any one of the following types: toner, gel, jelly mask, mud mask, lotion, cream, lipstick, foundation, pressed powder, face powder, cleansing oil, cleansing milk, facial cleanser, body wash, shampoo, hair conditioner, sunscreen, hand cream, nail polish, perfume, essence, and facial mask. In some embodiments, the cosmetic or the cosmeceutical may further contain acceptable ingredients for external products as required. In some embodiments, the acceptable ingredients for external products may be, for example, an emulsifier, a penetration enhancer, an emollient, a solvent, an excipient, an antioxidant, or a combination thereof.

Example 1: Preparation of Dan Feng Peony Extract

Raw materials: flowers of Dan Feng peony A (scientific name: *Paeonia ostii*) and flowers of Dan Feng peony B (scientific name: *Paeonia Suffruiticosa Andr.*), commercially available from Changsha Agricultural Construction Technology Co., Ltd.

The method for extracting a Dan Feng peony extract is that the flowers of the Dan Feng peony A were subjected to extraction in the flower-to-solvent volume ratio of 1:15 at 80±10° C. for 2 h to obtain a preliminary extract. Herein, the solvent was water. Next, the preliminary extract was cooled to room temperature, the preliminary extract was then filtered with a 400 mesh filter to obtain a filtrate, and the filtrate was then concentrated under reduced pressure at 55±10° C. to obtain a concentrated liquid. Herein, the concentrated liquid is Dan Feng peony extract A.

Then, the flowers of the Dan Feng peony B were prepared into Dan Feng peony extract B according to the same method.

2.5 mL of the Dan Feng peony extract A was added into 50 mL of drinking water to obtain Dan Feng peony extract C with a concentration of 0.05 mg/mL.

Example 2: Hyaluronic Acid Production Experiment

Materials:

A cell strain is human primary epidermal keratinocytes (HPEKp) commercially available from CELLnTEC (Switzerland) with a model of HPEK-50.

A culture medium is a keratinocyte-serum-free medium (keratinocyte-SFM) commercially available from Gibco, USA, No. #10724-011.

A human hyaluronic acid (HA) ELISA kit commercially available from Cusabio Biotech.

An ELISA reader commercially available from Bio Tek, USA.

Test process:

The HPEKp was inoculated in a culture plate containing 2 mL of culture medium per well in a density of $1 \times 10^4$ cells per well. The Dan Feng peony extract A with a concentration of 0.25 mg/mL was additionally added to the culture medium of an experimental group. There were no other substances added to the culture medium of a control group. Each group was repeated for three times and then cultured at 37° C. for 24 h.

Next, 100 μL of the culture medium from each well was added into a pre-coated ELISA plate to culture at 37° C. for 2 h. Then, the culture medium in each well was removed, and each well was not washed. 100 μL of biotin-antibody was added into each well to culture at 37° C. for 1 h. After the reaction was completed, the culture medium in each well was removed, each well was washed with 200 μL of wash buffer and then allowed to stand for 2 min after each wash, and this step was repeated for three times. After the last wash is completed, all remaining wash buffer was removed by suction.

Then, 100 μL of HRP-avidin was added into each well to culture at 37° C. for 1 h. After the reaction was completed, the culture medium in each well was removed, each well was washed with 200 μL of wash buffer and then allowed to stand for 2 min after each wash, and this step was repeated for three times. After the last wash is completed, all remaining wash buffer was removed by suction.

90 μL of TMB substrate was added into each well to react in the dark at 37° C. for 15-30 min. 50 μL of stop solution was added into each well, and the culture plate was gently tapped to ensure adequate mixing. Finally, the absorbance at 450 nm was measured in each well within 5 min by using an ELISA reader.

As shown in FIG. 1, the obtained results were analyzed by student t-test using Excel software to determine whether there is a statistically significant difference between two sample groups. (In the figure, "*" represents a p value less than 0.05, "" represents a p value less than 0.01, and "*" represents a p value less than 0.001. The more "*" there is, the more significant the statistical difference is.)

Referring to FIG. 1, The HPEKp in the control group is not processed through Dan Feng peony extraction, that is, it is under normal physiological metabolism, and the hyaluronic acid production thereof is set to 100%. The HPEKp in the experimental group is processed through Dan Feng peony extraction for 2 h, and the hyaluronic acid production thereof, compared to the control group, is 117.3%. It can be learned that the Dan Feng peony extract can significantly promote the HPEKp to produce hyaluronic acid within just 2 h.

Example 3: Expression of Hyaluronic Acid Secretion-Related Gene

The materials and test process in this example are the same as Example 2.

Control group: only a culture medium was added to culture at 37° C. for 24 h.

Experimental group: the Dan Feng peony extract A with a concentration of 0.125 mg/mL was added to culture at 37° C. for 24 h.

Figure 2:
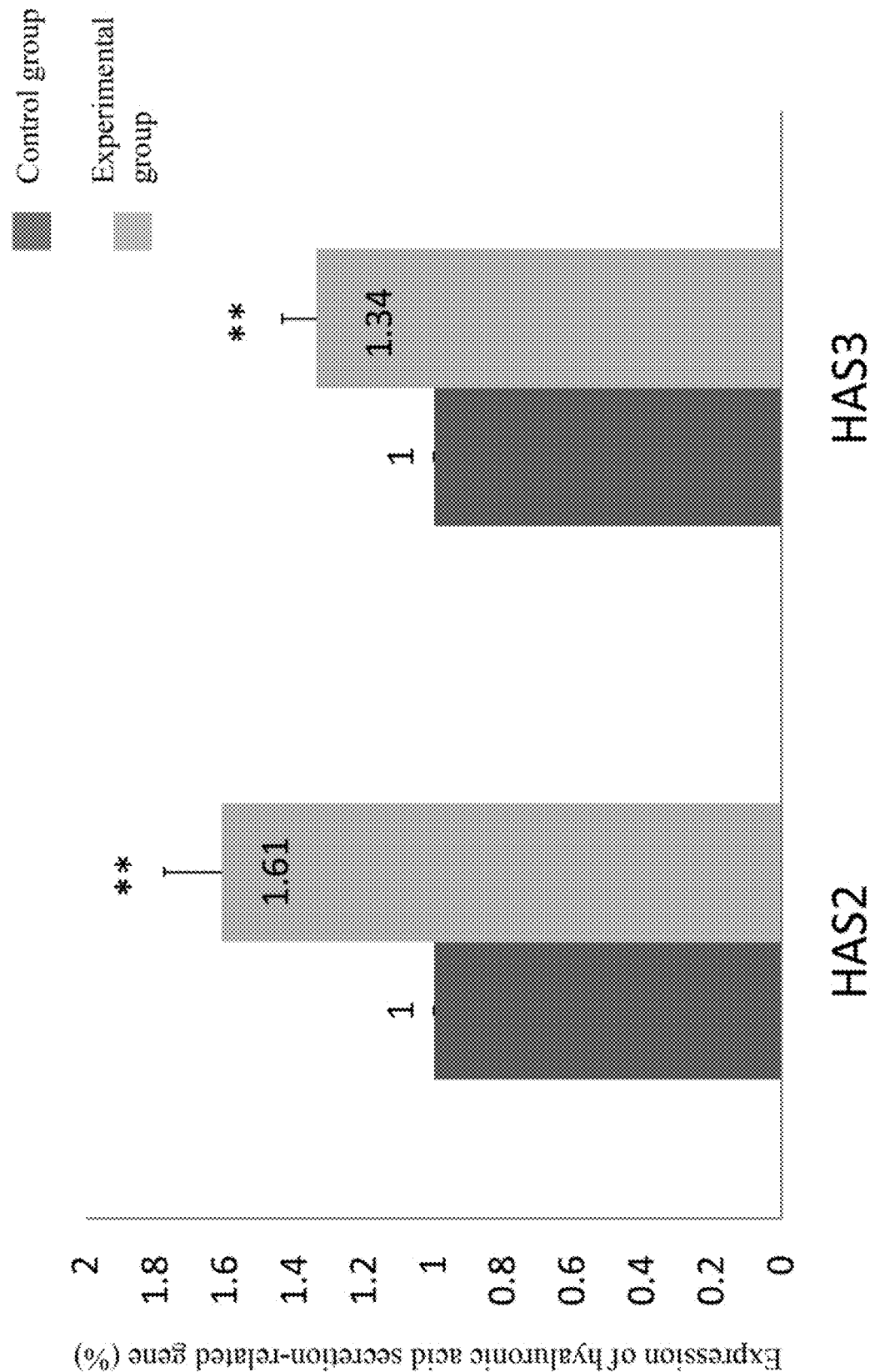
FIG. 2 is a graph showing an experimental result of a Dan Feng peony extract promoting the expression of hyaluronic acid secretion-related gene.

Herein, as shown in FIG. 2, the quantitative real-time reverse transcription polymerase chain reaction with cDNA can indirectly quantify the mRNA expression level of each gene, and then infer the expression level of the protein encoded by each gene.

TABLE 1

| Target gene | Primer name | Sequence NO. | Sequence | Length |
|---|---|---|---|---|
| HAS2 | HAS2-F | SEQ ID NO: 1 | AAGAACAACTTC CACGAAAAGGG | 23 |
|  | HAS2-R | SEQ ID NO: 2 | CGCAGCAACTTC CATGAGG | 19 |
| HAS3 | HAS3-F | SEQ ID NO: 3 | AAGAACAACTTC CACGAAAAGGG | 23 |
|  | HAS3-R | SEQ ID NO: 4 | CGCAGCAACTTC CATGAGG | 19 |
| GAPDH | GAPDH-F | SEQ ID NO: 5 | CTGGGCTACACT GAGCACC | 19 |
|  | GAPDH-R | SEQ ID NO: 6 | AAGTGGTCGTTG AGGGCAATG | 21 |

Herein, the relative expression level of the target gene was determined by the 2-ΔΔCT method. The relative expression level is defined as a multiple of the RNA expression level of a target gene relative to the corresponding gene in the control group. This method uses the cycle threshold (CT) of the GAPDH gene as the CT of the reference gene of the internal control, and calculates the fold change according to the following formula: ΔCT=CT of target gene in experimental group or control group—CT of internal control ΔΔCT=ΔCT in experimental group—ΔCT in control group Fold change=2-ΔΔCT average.

Referring to FIG. 2, when the expression level of the HAS2 gene in the control group is regarded as 1, the expression level of the HAS2 gene in the experimental group relative to the control group is 1.61, indicating that, compared with the control group, the expression level of the HAS2 gene in the experimental group significantly increases; and when the expression level of the HAS3 gene in the control group is regarded as 1, the expression level of the HAS3 gene in the experimental group relative to the control group is 1.34, indicating that, compared with the control group, the expression level of the HAS3 gene in the experimental group significantly increases.

It is to be noted that the data in FIG. 2 is presented by relative magnification, that is, the quantitative result of the control group is regarded as 1 to convert the quantitative result of the experimental group into the expression level relative to the control group. The standard deviation is calculated by using the STDEV formula of Excel software, and whether there is a statistically significant difference is analyzed by one-tailed student t-test in Excel software. In the figure, "*" represents a p value less than 0.05 relative to the control group, "" represents a p value less than 0.01 relative to the control group, and "*" represents a p value less than 0.001 relative to the control group.

It can be learned that skin cells treated with the Dan Feng peony extract can significantly increase the expression level of hyaluronic acid secretion-related gene. That is, the Dan Feng peony extract can effectively promote autogenous secretion of cells or synthesis of hyaluronic acid, and increase the content of hyaluronic acid in cells.

Example 4: Expression of Skin Keratinocyte Structure Maintenance-Related Gene

The materials and test process in this example are the same as Example 2.

Control group: only a culture medium was added to culture at 37° C. for 24 h.

Experimental group: the Dan Feng peony extract A with a concentration of 0.125 mg/mL was added to culture at 37° C. for 24 h.

Figure 3:
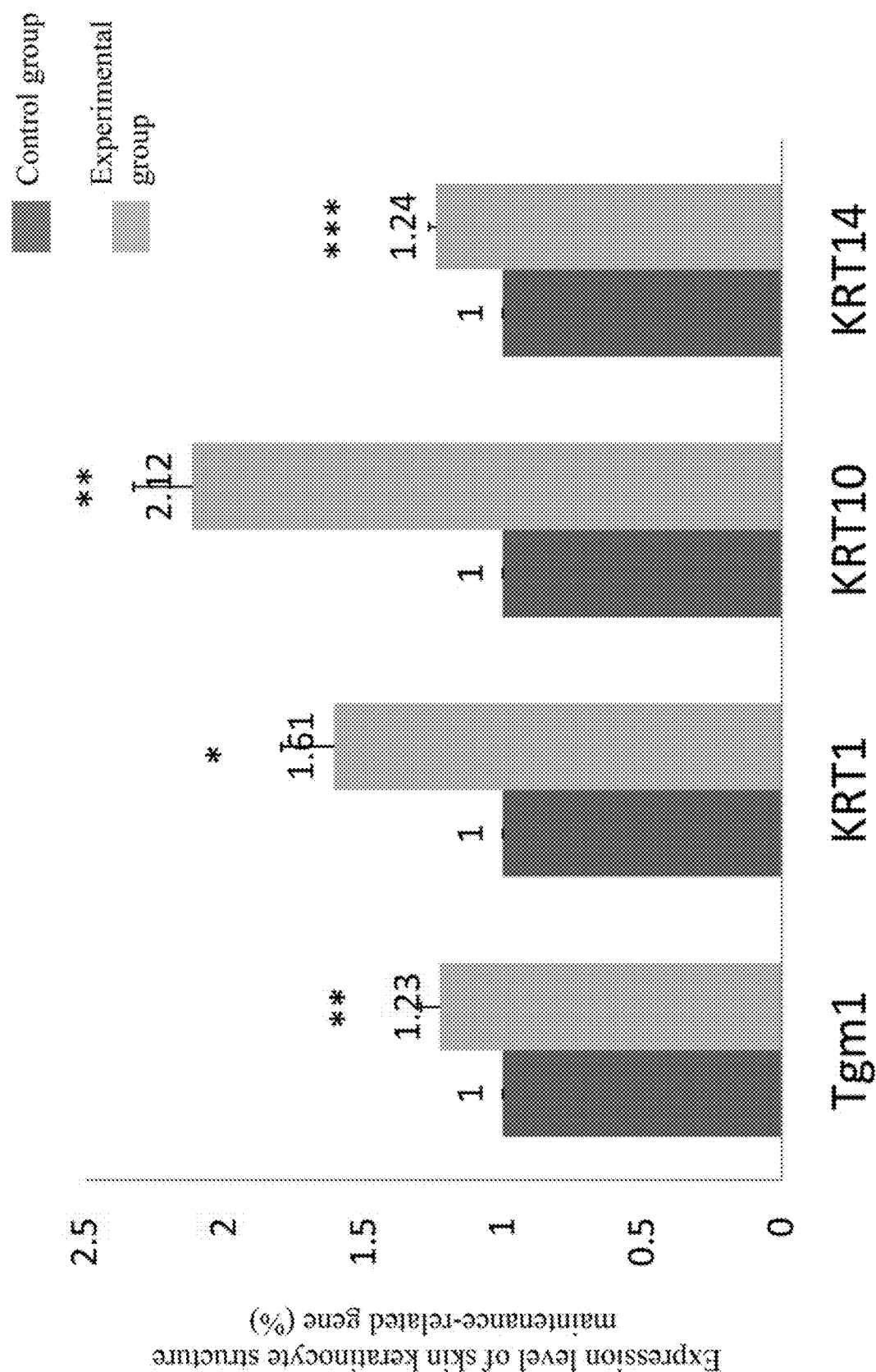
FIG. 3 is a graph showing an experimental result of a Dan Feng peony extract promoting the expression of skin keratinocyte structure maintenance-related gene.

Herein, as shown in FIG. 3, the quantitative real-time reverse transcription polymerase chain reaction with cDNA can indirectly quantify the mRNA expression level of each gene, and then infer the expression level of the protein encoded by each gene.

TABLE 2

| Target gene | Primer name | Sequence NO. | Sequence | Length |
|---|---|---|---|---|
| TGM1 | TGM1-F | SEQ ID NO: 7 | GATCGCATCAC CCTTGAGTTAC | 22 |
|  | TGM1-R | SEQ ID NO: 8 | GCAGGTTCAGA TTCTGCCC | 19 |
| KRT1 | KRT1-F | SEQ ID NO: 9 | AGAGTGGACCA ACTGAAGAGT | 21 |
|  | KRT1-R | SEQ ID NO: 10 | ATTCTCTGCAT TTGTCCGCTT | 21 |
| KRT10 | KRT10-F | SEQ ID NO: 11 | TCCTACTTGGA CAAAGTTCGGG | 22 |
|  | KRT10-R | SEQ ID NO: 12 | CCCCTGATGTG AGTTGCCA | 19 |
| KRT14 | KRT14-F | SEQ ID NO: 13 | TTCTGAACGAG ATGCGTGAC | 20 |
|  | KRT14-R | SEQ ID NO: 14 | GCAGCTCAATC TCCAGGTTC | 20 |
| TBP | TBP-F | SEQ ID NO: 15 | TATAATCCCAA GCGGTTTGC | 20 |

TABLE 2-continued

| Target gene | Primer name | Sequence NO. | Sequence | Length |
|---|---|---|---|---|
|  | TBP-R | SEQ ID NO: 16 | GCTGGAAAACC CAACTTCTG | 20 |

Herein, the relative expression level of the target gene was determined by the 2-$\Delta\Delta CT$ method. The relative expression level is defined as a multiple of the RNA expression level of a target gene relative to the corresponding gene in the control group. This method uses the cycle threshold (CT) of the TBP gene as the CT of the reference gene of the internal control, and calculates the fold change according to the following formula: $\Delta CT = CT$ of target gene in experimental group or control group—CT of internal control $\Delta\Delta CT = \Delta CT$ in experimental group—$\Delta CT$ in control group Fold change=2-$\Delta\Delta Ct$ average.

Referring to FIG. 3, when the expression level of the TGM1 gene in the control group is regarded as 1, the expression level of the TGM1 gene in the experimental group relative to the control group is 1.23, indicating that, compared with the control group, the expression level of the TGM1 gene in the experimental group significantly increases;

when the expression level of the KRT1 gene in the control group is regarded as 1, the expression level of the KRT1 gene in the experimental group relative to the control group is 1.61, indicating that, compared with the control group, the expression level of the KRT1 gene in the experimental group significantly increases;

when the expression level of the KRT10 gene in the control group is regarded as 1, the expression level of the KRT10 gene in the experimental group relative to the control group is 2.12, indicating that, compared with the control group, the expression level of the KRT10 gene in the experimental group significantly increases; and when the expression level of the KRT14 gene in the control group is regarded as 1, the expression level of the KRT14 gene in the experimental group relative to the control group is 1.24, indicating that, compared with the control group, the expression level of the KRT14 gene in the experimental group significantly increases.

It is to be noted that the data in FIG. 3 is presented by relative magnification, that is, the quantitative result of the control group is regarded as 1 to convert the quantitative result of the experimental group into the expression level relative to the control group. The standard deviation is calculated by using the STDEV formula of Excel software, and whether there is a statistically significant difference is analyzed by one-tailed student t-test in Excel software. In the figure, "*" represents a p value less than 0.05 relative to the control group, "" represents a p value less than 0.01 relative to the control group, and "*" represents a p value less than 0.001 relative to the control group.

It can be learned that skin cells treated with the Dan Feng peony extract can significantly increase the expression level of skin keratinocyte structure maintenance-related gene. That is, the Dan Feng peony extract can effectively promote the structure of the stratum corneum to be tight and prevent skin water loss, and has the effect of skin moisturizing.

Example 5: Enhancing Expression of Skin Moisturizing Fiber-Related Gene

The materials and test process in this example are the same as Example 2.

Control group: only a culture medium was added to culture at 37° C. for 24 h.

Experimental group: the Dan Feng peony extract A with a concentration of 0.125 mg/mL was added to culture at 37° C. for 24 h.

Figure 4:
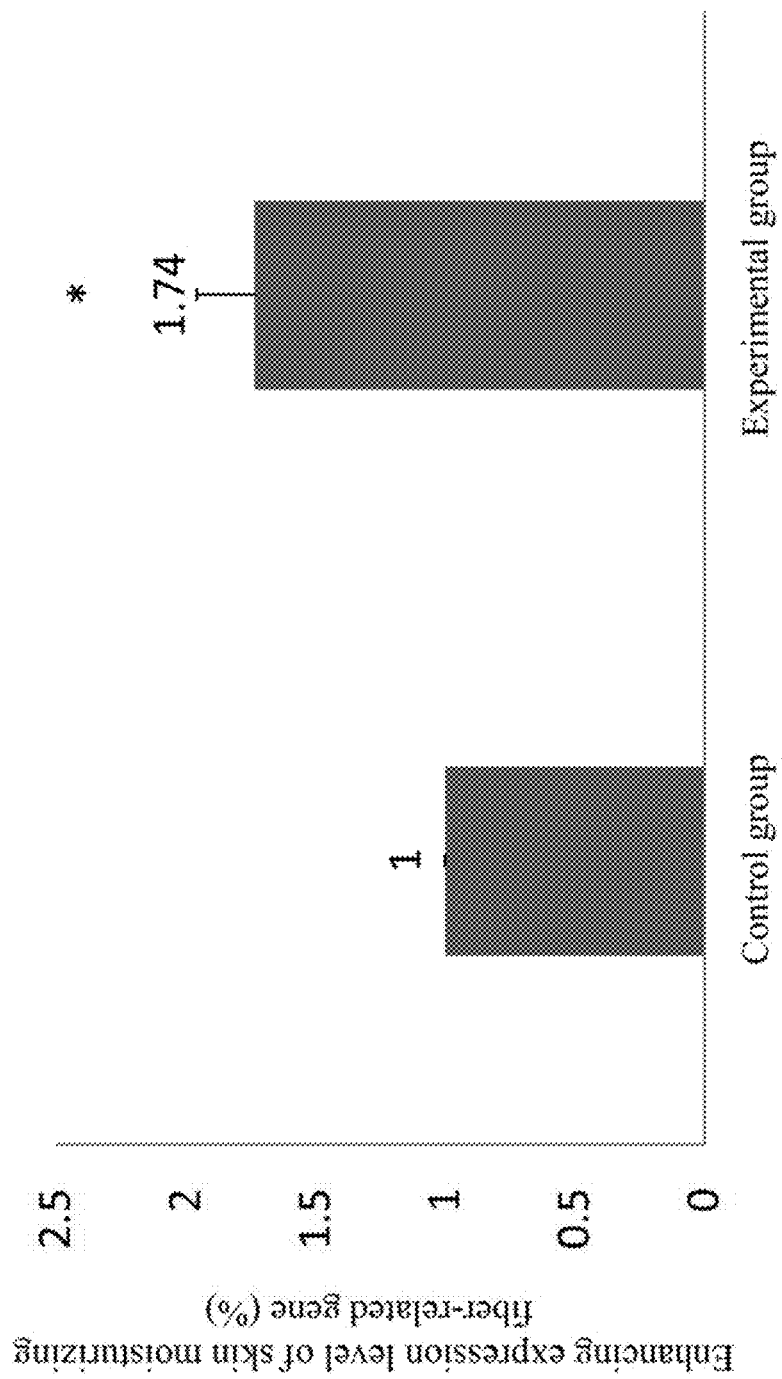
FIG. 4 is a graph showing an experimental result of a Dan Feng peony extract enhancing the expression of skin moisturizing fiber-related gene.

Herein, as shown in FIG. 4, the quantitative real-time reverse transcription polymerase chain reaction with cDNA can indirectly quantify the mRNA expression level of each gene, and then infer the expression level of the protein encoded by each gene.

TABLE 3

| Target gene | Primer name | Sequence NO. | Sequence | Length |
|---|---|---|---|---|
| FLG | FLG-F | SEQ ID NO: 17 | GGCAAATCCTG AAGAATCCA | 20 |
|  | FLG-R | SEQ ID NO: 18 | TGCTTTCTGTG CTTGTGTCC | 20 |
| TBP | TBP-F | SEQ ID NO: 15 | TATAATCCCAA GCGGTTTGC | 20 |
|  | TBP-R | SEQ ID NO: 16 | GCTGGAAAACC CAACTTCTG | 20 |

Herein, the relative expression level of the target gene was determined by the 2–ΔΔCT method. The relative expression level is defined as a multiple of the RNA expression level of a target gene relative to the corresponding gene in the control group. This method uses the cycle threshold (CT) of the TBP gene as the CT of the reference gene of the internal control, and calculates the fold change according to the following formula: ΔCT=CT of target gene in experimental group or control group—CT of internal control ΔΔCT=ΔCT in experimental group—OCT in control group Fold change=2–ΔΔCt average.

Referring to FIG. 4, when the expression level of the FLG gene in the control group is regarded as 1, the expression level of the FLG gene in the experimental group relative to the control group is 1.74, indicating that, compared with the control group, the expression level of the FLG gene in the experimental group significantly increases.

It is to be noted that the data in FIG. 4 is presented by relative magnification, that is, the quantitative result of the control group is regarded as 1 to convert the quantitative result of the experimental group into the expression level relative to the control group. The standard deviation is calculated by using the STDEV formula of Excel software, and whether there is a statistically significant difference is analyzed by one-tailed student t-test in Excel software. In the figure, "*" represents a p value less than 0.05 relative to the control group, "" represents a p value less than 0.01 relative to the control group, and "*" represents a p value less than 0.001 relative to the control group.

It can be learned that skin cells treated with the Dan Feng peony extract can significantly increase the expression level of skin moisturizing fiber-related gene. That is, the Dan Feng peony extract can effectively promote the proliferation of filaggrin in the skin, and then has the effect of skin moisturizing.

Example 6: Expression of Skin Cell Moisture Content-Related Gene

The materials and test process in this example are the same as Example 2.

Control group: only a culture medium was added to culture at 37° C. for 24 h.

Experimental group: the Dan Feng peony extract A with a concentration of 0.125 mg/mL was added to culture at 37° C. for 24 h.

Figure 5:
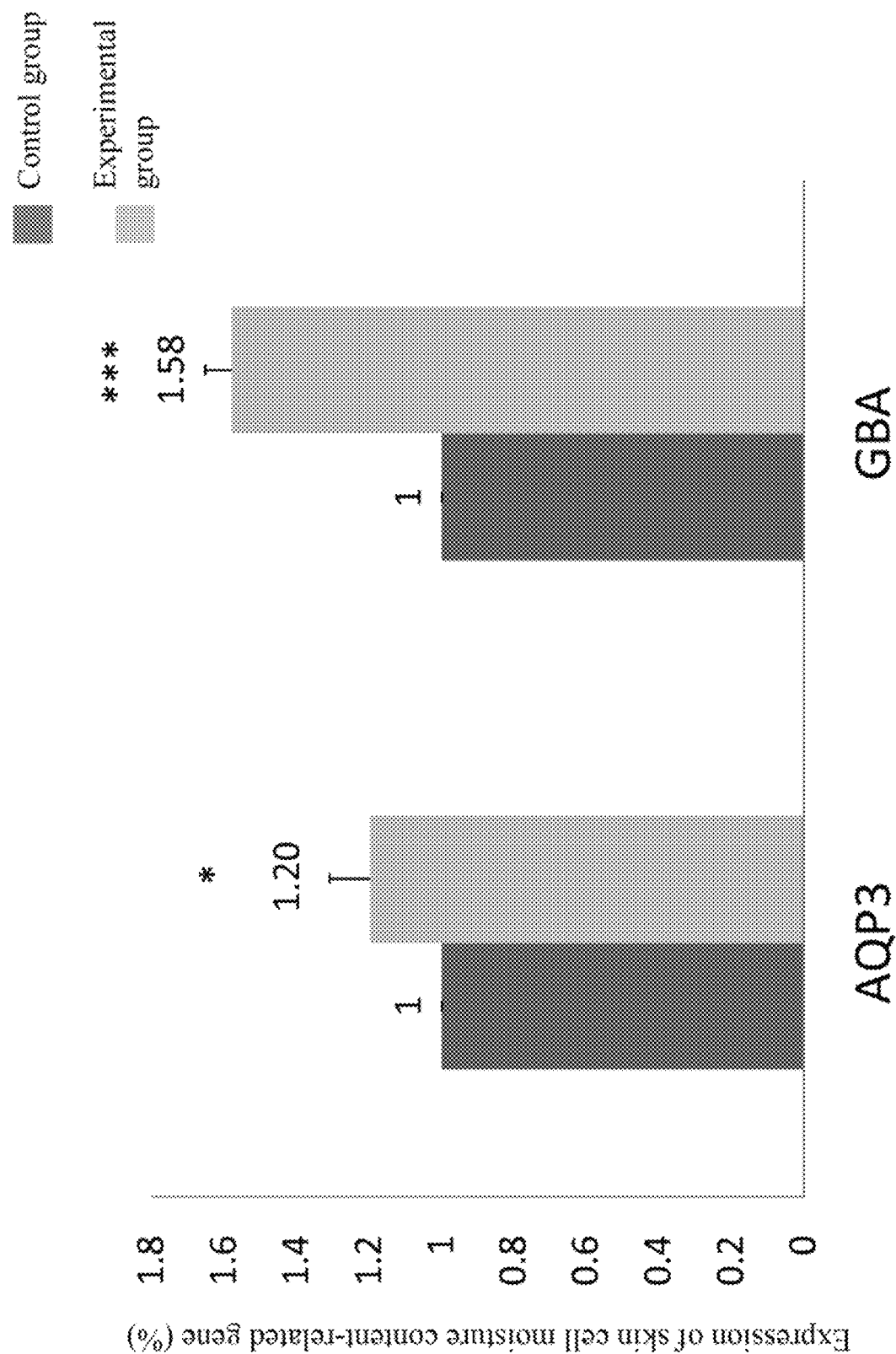
FIG. 5 is a graph showing an experimental result of a Dan Feng peony extract promoting the expression of skin cell moisture content regulation-related gene.

Herein, as shown in FIG. 5, the quantitative real-time reverse transcription polymerase chain reaction with cDNA can indirectly quantify the mRNA expression level of each gene, and then infer the expression level of the protein encoded by each gene.

TABLE 4

| Target gene | Primer name | Sequence NO. | Sequence | Length |
|---|---|---|---|---|
| AQP3 | AQP3-F | SEQ ID NO: 19 | GGGGAGATGCTC CACATCC | 19 |
|  | AQP3-R | SEQ ID NO: 20 | AAAGGCCAGGTT GATGGTGAG | 21 |
| GBA | GBA-F | SEQ ID NO: 21 | TCCAGTTGCACA ACTTCAGC | 20 |
|  | GBA-R | SEQ ID NO: 22 | TTGTGCTCAGCA TAGGCATC | 20 |
| TBP | TBP-F | SEQ ID NO: 15 | TATAATCCCAAG CGGTTTGC | 20 |
|  | TBP-R | SEQ ID NO: 16 | GCTGGAAAACCC AACTTCTG | 20 |

Herein, the relative expression level of the target gene was determined by the 2–ΔΔCT method. The relative expression level is defined as a multiple of the RNA expression level of a target gene relative to the corresponding gene in the control group. This method uses the cycle threshold (CT) of the TBP gene as the CT of the reference gene of the internal control, and calculates the fold change according to the following formula: ΔCT=CT of target gene in experimental group or control group—CT of internal control ΔΔCT=ΔCT in experimental group—ΔCT in control group Fold change=2–ΔΔCt average.

Referring to FIG. 5, when the expression level of the AQP3 gene in the control group is regarded as 1, the expression level of the AQP3 gene in the experimental group relative to the control group is 1.20, indicating that, compared with the control group, the expression level of the AQP3 gene in the experimental group significantly increases; and when the expression level of the GBA gene in the control group is regarded as 1, the expression level of the GBA gene in the experimental group relative to the control group is 1.58, indicating that, compared with the control group, the expression level of the GBA gene in the experimental group significantly increases.

It is to be noted that the data in FIG. 5 is presented by relative magnification, that is, the quantitative result of the control group is regarded as 1 to convert the quantitative result of the experimental group into the expression level relative to the control group. The standard deviation is calculated by using the STDEV formula of Excel software, and whether there is a statistically significant difference is analyzed by one-tailed student t-test in Excel software. In the figure, "*" represents a p value less than 0.05 relative to the control group, "**" represents a p value less than 0.01 relative to the control group, and "***" represents a p value less than 0.001 relative to the control group.

It can be learned that skin cells treated with the Dan Feng peony extract can significantly increase the expression level of cell moisture content-related gene. That is, the Dan Feng peony extract can effectively promote the expression of transport proteins on the cell membranes and increase the moisture content in the cells.

Example 7: Human Subject Experiment of Dan Feng Peony Extract Food

Subjects: 8 subjects (adults with dry skin, where the dry skin refers to skin tightness, scaling, dry itching, etc.).

Test items and instruments:

1. Skin hydration: the skin hydration detection probe Comeometer® CM825 (C+K Multi Probe Adapter System, Germany) commercially available from Courage+Khazaka Electronic is used to detect the facial skin of the subjects. The detection probe is used based on the principle of capacitance for measurement. When the water content changes, the capacitance value of the skin also changes, so that the water content of the skin surface can be analyzed by measuring the capacitance value of the skin.

2. TEWL: the skin water loss detection probe Tewameter® 300 (C+K Multi Probe Adapter System, Germany) commercially available from Courage+Khazaka Electronic is used to detect the facial skin of the subjects. The detection probe uses a cylindrical cavity with open ends to form a relatively stable test environment on the skin surface, and measures the water vapor pressure gradient at two different points to calculate the amount of water evaporated through the epidermis, so as to measure the water loss on the skin surface.

3. Skin elasticity: the skin elasticity detection probe Cutometer® MPA580 (C+K Multi Probe Adapter System, Germany) commercially available from Courage+Khazaka Electronic is used to detect the facial skin of the same subject before and after drinking. The test principle is that, based on the principle of suction and stretching, a negative pressure is generated on the surface of the skin to be tested to suck the skin into a test probe, the depth of the skin sucked into the probe is detected through the optical test system, and the skin elasticity and firmness are calculated by software analysis.

4. Skin wrinkles: the detection was carried out by using the VISIA high-end digital skin quality detector commercially available from Canfield, USA. The facial skin of the same subject before and after drinking was photographed through a high-resolution camera lens. The change of the skin shadow is detected by standard white light irradiation to detect the texture position and obtain a value that can represent the smoothness of the skin.

5. Skin texture: the VISIA high-end digital skin quality detector commercially available from Canfield, USA is used to detect the facial skin of the subjects. The principle is to shoot a high-resolution skin image with visible light, and analyze the roughness according to the unevenness of the skin by using built-in software. The higher the measurement value is, the rougher the skin is.

6. The subjects rated the severity of skin dryness, tightness, dullness, and overall skin condition with a questionnaire.

Test method:

8 subjects were allowed to drink 4 mL of the Dan Feng peony extract C prepared in the foregoing example daily for 4 weeks. The facial skin conditions of each subject before drinking (week 0, also referred to as a control group) and 4 weeks after drinking (week 4, also referred to as an experimental group) were measured by using the foregoing instruments, and each subject filled in a questionnaire for scoring. In the questionnaire, 0 points means no trouble, 1 point means mild, 2 points means medium, 3 points means severe, and 4 points means very severe. The score of each subject in week 0 was converted into 100%, and the score in week 4 was scored by the conversion formula (W4 score−W0 score)/W0 score*100+100.

Herein, when the detection was carried out by using the instruments before and after drinking, the temperature and humidity of the detection region of the subjects were consistent to reduce the influence of external temperature and humidity on the skin.

The statistical significance difference between groups was counted and analyzed through student t-test. In FIG. 6 to FIG. 11, "*" represents a p value less than 0.05 in comparison with the control group, indicating that there is a statistically significant difference between the experimental group and the control group.

It is to be noted that the data in the following figures is presented by relative magnification, that is, the quantitative result of the control group is regarded as 100% to convert the quantitative result of the experimental group into the expression level relative to the control group.

Figures 6, 7:
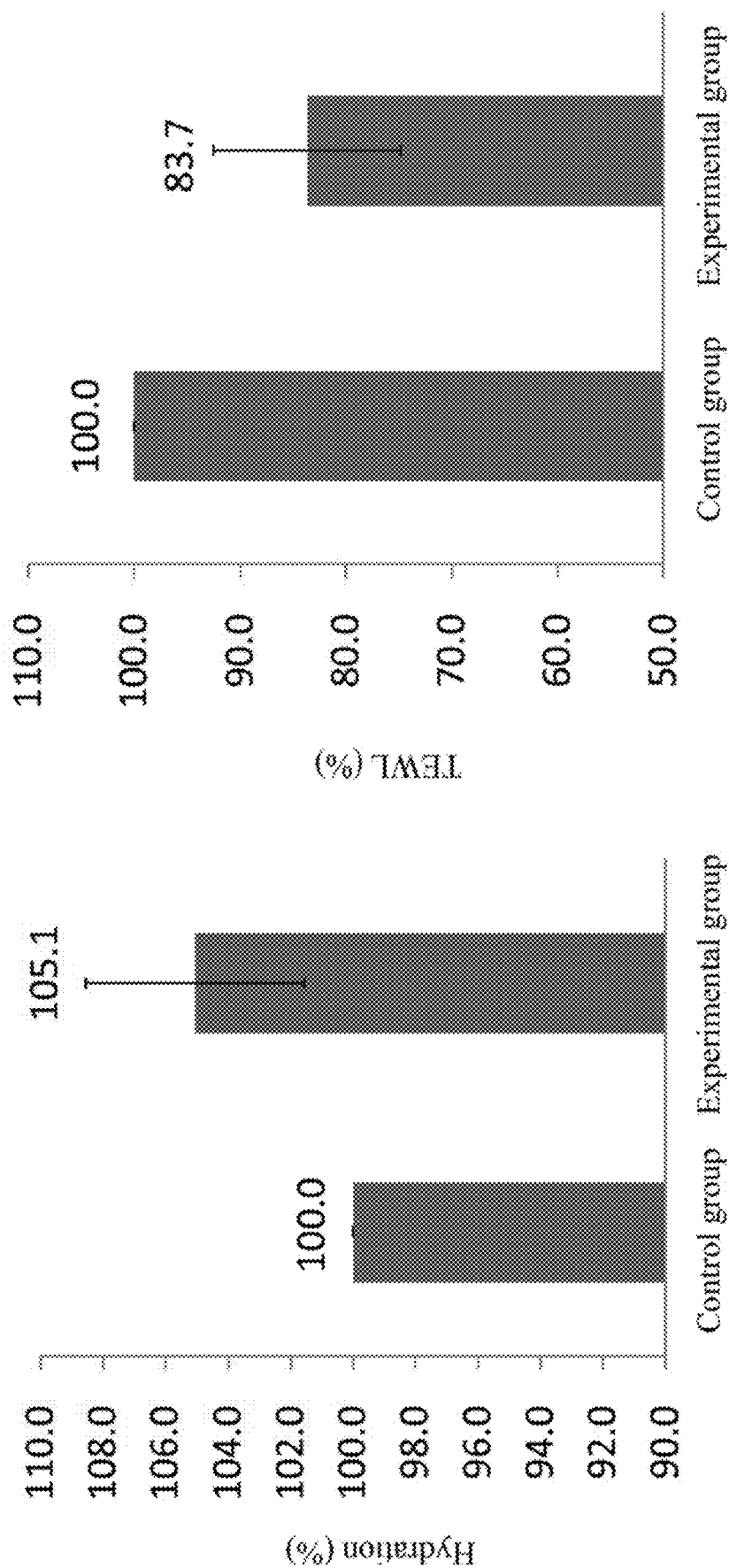
FIG. 6 is a graph showing an experimental result of the skin hydration in a human subject experiment using a Dan Feng peony extract.
FIG. 7 is a graph showing an experimental result of the skin TEWL ratio in a human subject experiment using a Dan Feng peony extract.

Test result:

Referring to FIG. 6, the average skin water content of the 8 subjects after four weeks of daily drinking of the Dan Feng peony extract was increased from 100% to 105.1%. That is, daily drinking of 4 mL of the Dan Feng peony extract effectively increased the skin water content by 5.1%.

Referring to FIG. 7, the average TEWL of the 8 subjects after four weeks of daily drinking of the Dan Feng peony extract was reduced from 100% to 83.7%. That is, daily drinking of 4 mL of the Dan Feng peony extract effectively reduced the TEWL by 16.3%.

Figures 8, 9:
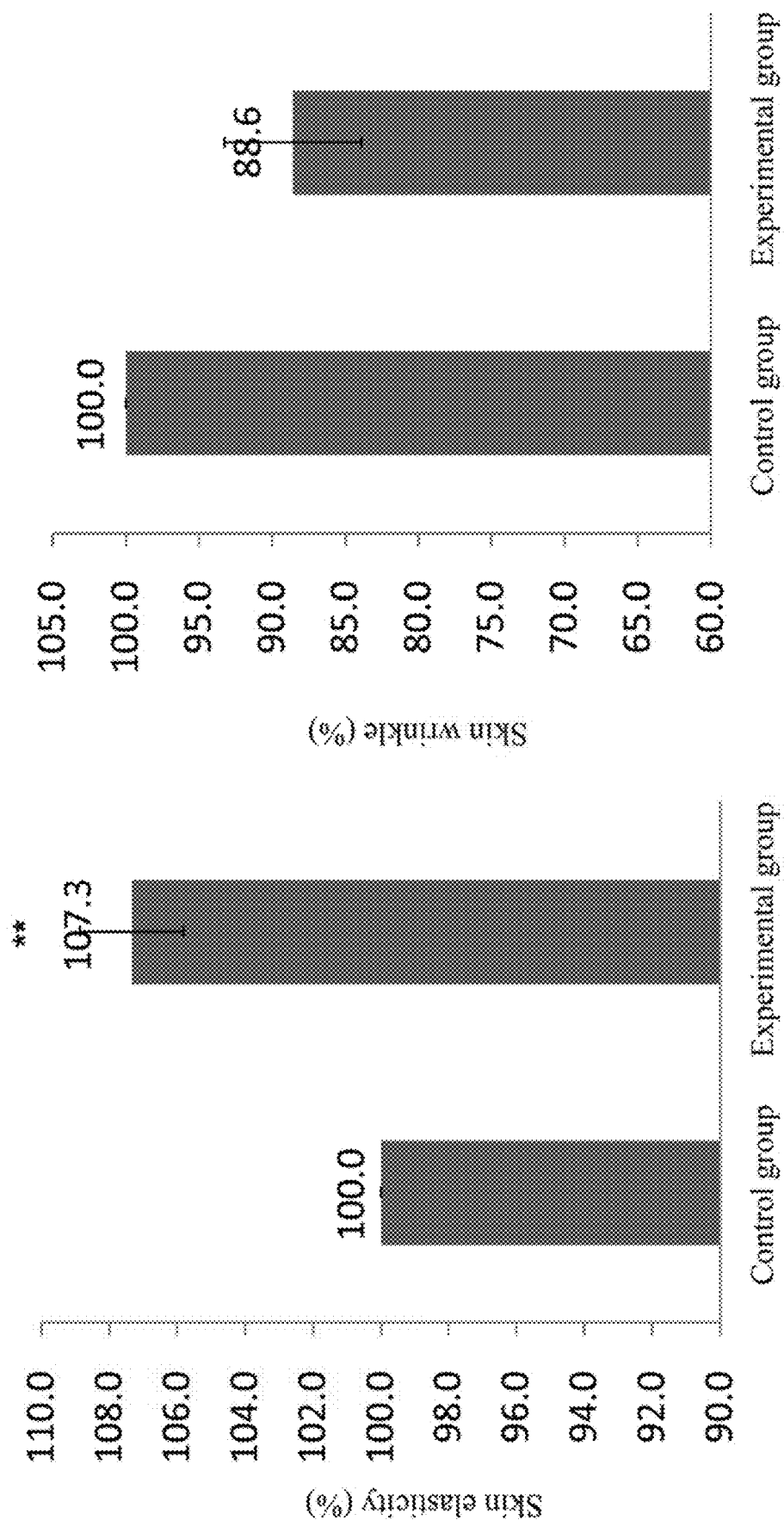
FIG. 8 is a graph showing an experimental result of the skin elasticity improvement in a human subject experiment using a Dan Feng peony extract.
FIG. 9 is a graph showing an experimental result of the skin wrinkle improvement in a human subject experiment using a Dan Feng peony extract.

Referring to FIG. 8, the average skin elasticity of the 8 subjects after four weeks of daily drinking of the Dan Feng peony extract was increased from 100% to 107.3%. That is, daily drinking of 4 mL of the Dan Feng peony extract significantly increased the skin elasticity by 7.3%.

Referring to FIG. 9, the average skin wrinkles of the 8 subjects after four weeks of daily drinking of the Dan Feng peony extract was reduced from 100% to 88.6%. That is, daily drinking of 4 mL of the Dan Feng peony extract effectively reduced the skin wrinkles by 11.4%.

Figure 10:
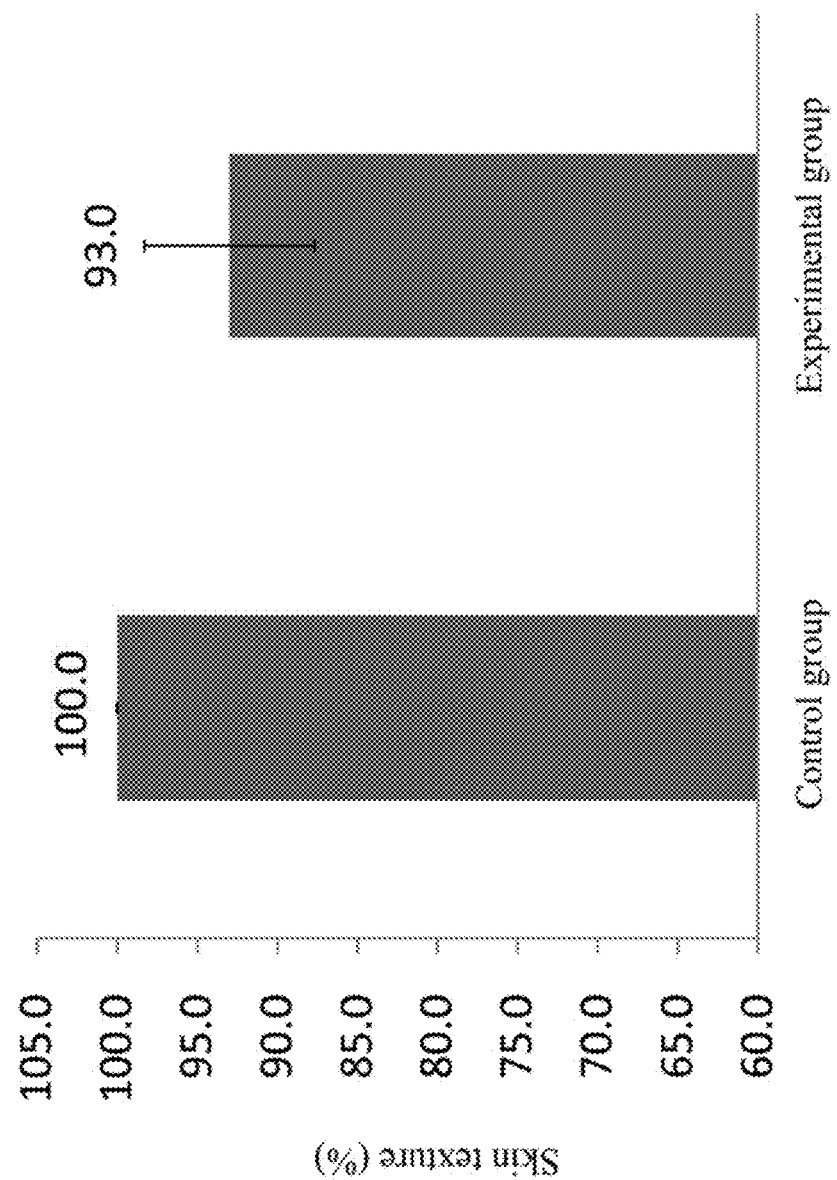
FIG. 10 is a graph showing an experimental result of the skin texture improvement in a human subject experiment using a Dan Feng peony extract.

Referring to FIG. 10, the average skin texture (also referred to as roughness) of the 8 subjects after four weeks of daily drinking of the Dan Feng peony extract was reduced from 100% to 93.0%. That is, daily drinking of 4 mL of the Dan Feng peony extract effectively reduced the skin texture by 7%.

Figure 11:
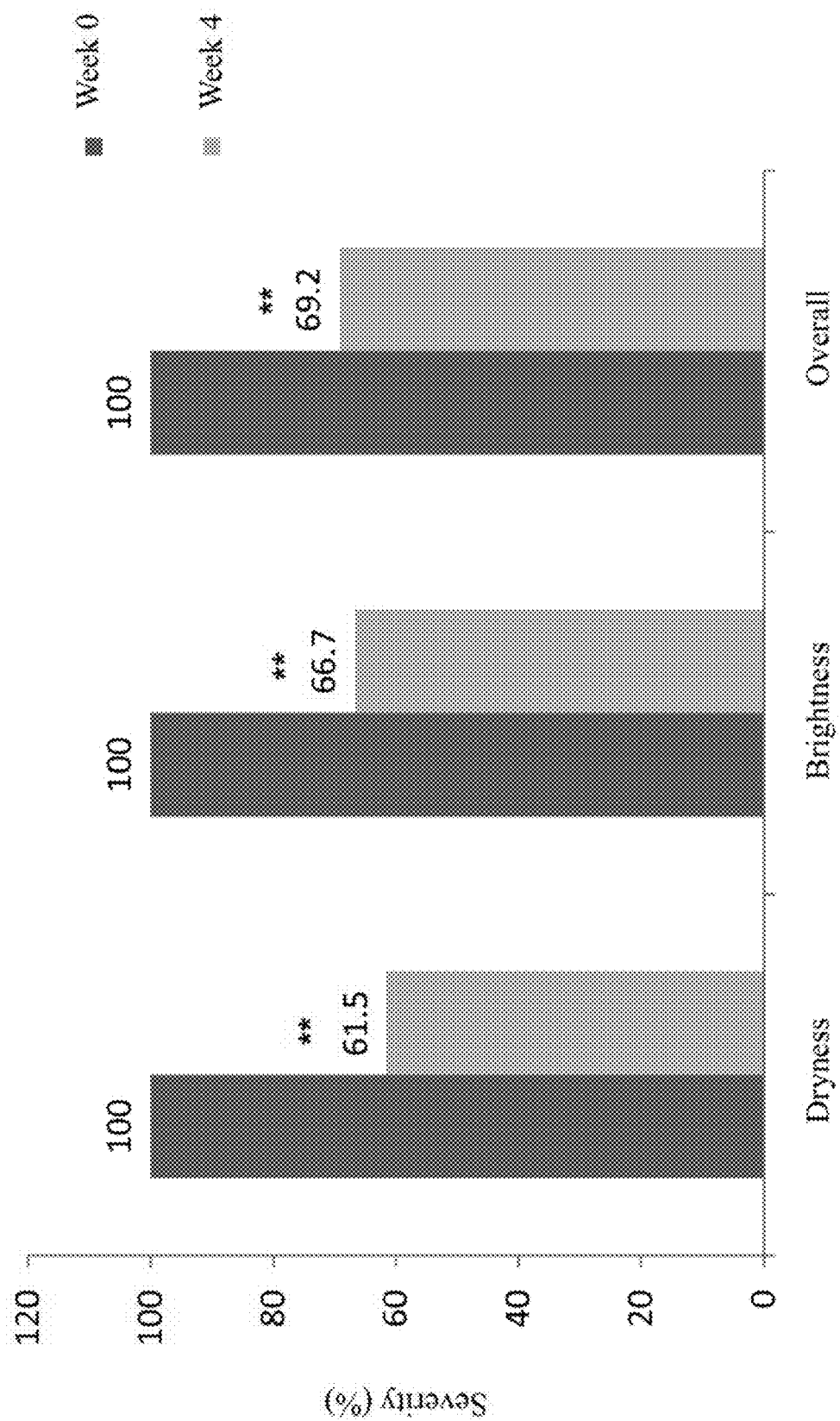
FIG. 11 is a graph showing an experimental result of questionnaire statistics in a human subject experiment using a Dan Feng peony extract.

Referring to FIG. 11, the 8 subjects after four weeks of daily drinking of the Dan Feng peony extract rated the severity of skin dryness and tightness, and the severity of skin dryness and tightness was reduced from 100% to 61.5%. That is, daily drinking of 4 mL of the Dan Feng peony extract made the subjects feel improvement of their skin dryness and tightness.

Still referring to FIG. 11, the 8 subjects after four weeks of daily drinking of the Dan Feng peony extract rated the severity of dullness, and the severity of skin dullness was reduced from 100% to 66.7%. That is, daily drinking of 4 mL of the Dan Feng peony extract made the subjects feel improvement of their skin dullness.

Still referring to FIG. 11, the 8 subjects after four weeks of daily drinking of the Dan Feng peony extract scored the overall poor skin condition. The feeling of overall poor skin condition was reduced from 100% to 69.2%. That is, daily drinking of 4 mL of the Dan Feng peony extract made the subjects feel improvement of their overall skin condition.

Example 8: Human Subject Experiment of Dan Feng peony Extract Topical Composition Facial mask ingredients and production:
First, an essence containing the Dan Feng peony extract was produced with a formula including: 0.2 wt % of xanthan gum, 0.6 wt % of hydroxyacetophenone, 5 wt % of 1,3-butanediol, 0.1 wt % of triethanolamine, 0.6 wt % of hexanediol, 0.5 wt % of Dan Feng peony extract, and the rest of water. The Dan Feng peony extract was the Dan Feng peony extract B prepared by the method in Example 1.

Then, the facial mask with the Dan Feng peony extract was made by soaking a facial mask cloth in the essence containing the Dan Feng peony extract to make the essence be fully absorbed, and the facial mask in a control group was made by soaking the same type of facial mask cloth in the essence containing water with an equal weight of the Dan Feng peony extract to replace it to make the essence be fully absorbed. In this example, each facial mask contained 20 mL of corresponding essence. That is, the facial mask with the Dan Feng peony extract was the facial mask containing 5% of the Dan Feng peony extract.

Test items and instruments:
1. Skin elasticity: the skin elasticity detection probe Cutometer® MPA580 (C+K Multi Probe Adapter System, Germany) commercially available from Courage+Khazaka Electronic is used to detect the facial skin of the subjects. The test principle is that, based on the principle of suction and stretching, a negative pressure is generated on the surface of the skin to be tested to suck the skin into a test probe, the depth of the skin sucked into the probe is detected through the optical test system, and the skin elasticity and firmness are calculated by software analysis.
2. Skin hydration: the skin hydration detection probe Corneometer® CM825 (C+K Multi Probe Adapter System, Germany) commercially available from Courage+Khazaka Electronic is used to detect the facial skin of the subjects. The detection probe is used based on the principle of capacitance for measurement. When the water content changes, the capacitance value of the skin also changes, so that the water content of the skin surface can be analyzed by measuring the capacitance value of the skin.
3. Skin brightness: the skin brightness detection probe Glossymeter GL200 (C+K Multi Probe Adapter System, Germany) commercially available from Courage+Khazaka Electronic is used to detect the facial skin of the subjects, and this instrument is used to test and calculate by direct reflection and diffuse reflection of the light irradiated on the skin surface. The higher the measurement value is, the brighter the skin is.
4. Skin redness: the VISIA high-end digital skin quality detector commercially available from Canfield, USA is used to detect the facial skin of the subjects. The facial skin is photographed by the RBX polarized light technology to detect deep blood vessels or hemoglobin of the skin. The higher the measurement value is, the more severe the redness of the skin is.

Subjects: 8 subjects (adults between 20 and 55 years old).
Test method:
After the subjects cleaned their full face, values of the left and right half of the face before the use of the facial mask were recorded by using the corresponding instruments and measurement methods according to the foregoing detection items, and the values before using was used as the benchmark (100%). Then, the Dan Feng peony extract facial mask and a placebo facial mask were applied on the right half face and the left half face of the subject respectively and taken off after 15 min, and then the right half face and the left half face were massaged with fingertips. After the facial mask was taken off for about 5 min, the measurement or photographing was carried out by using the corresponding instruments and measurement methods, and the obtained values were compared with the values before using of the right half face and the left half face, to obtain the values (%) after using. Herein, when the detection was carried out before and after using, the temperature and humidity of the detection region of the subjects were consistent to reduce the influence of external temperature and humidity on the skin.

Herein, the Dan Feng peony extract facial mask used on the right half face is an experimental group, and the placebo facial mask used on the left half face is a control group.

The statistical significance difference between groups was counted and analyzed through student t-test. In FIG. 12 to FIG. 15, "*" represents a p value less than 0.05 in comparison with the control group, indicating that there is a statistically significant difference between the experimental group and the control group.

It is to be noted that the data in the following figures is presented by relative magnification, that is, the quantitative result of the control group is regarded as 100% to convert the quantitative result of the experimental group into the expression level relative to the control group.

Figures 12, 13:
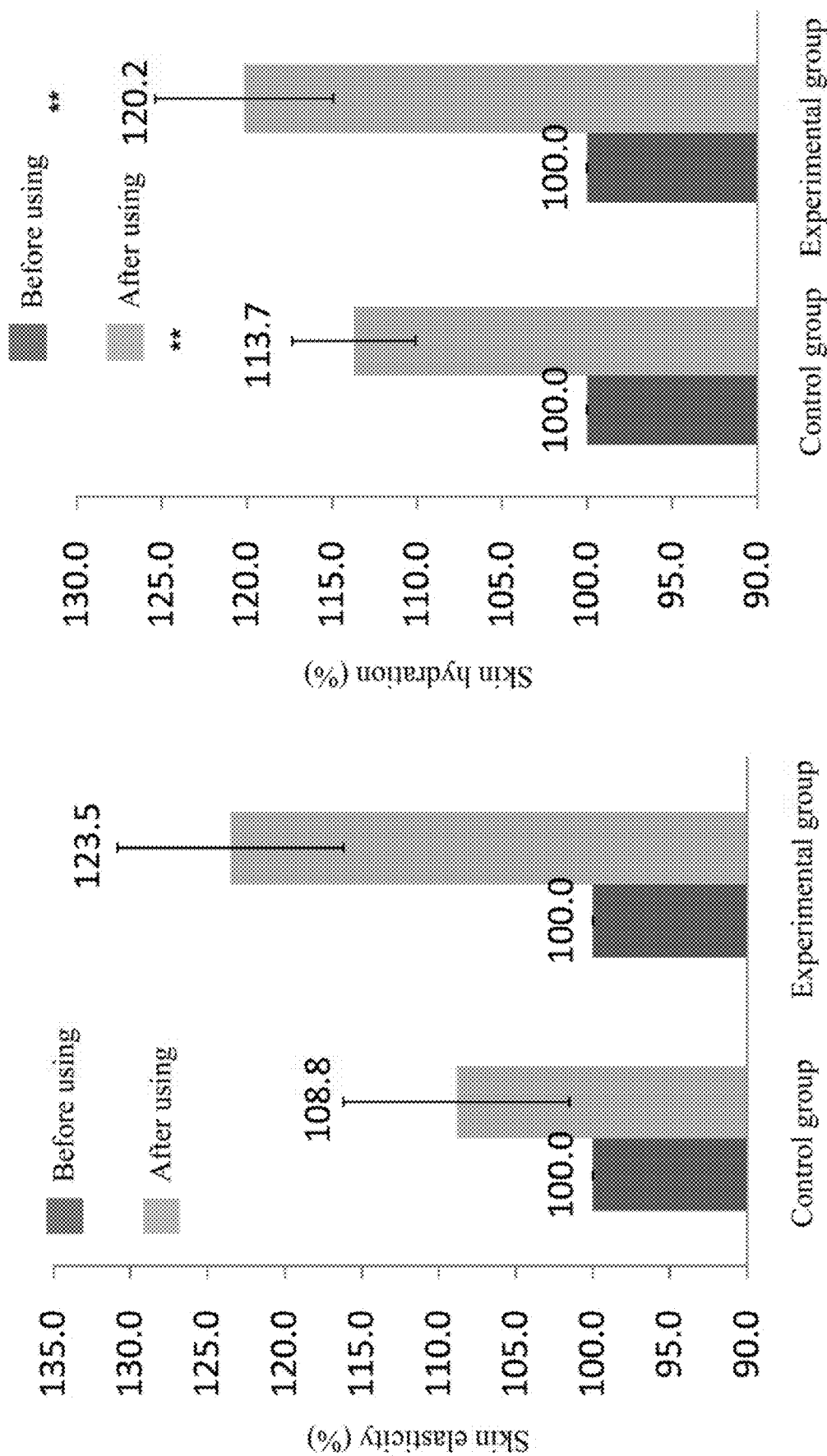
FIG. 12 is a graph showing an experimental result of the skin elasticity improvement in a human subject experiment using a facial mask containing a Dan Feng peony extract.
FIG. 13 is a graph showing an experimental result of the skin hydration improvement in a human subject experiment using a facial mask containing a Dan Feng peony extract.

Test result:
Referring to FIG. 12, the average skin elasticity of the 8 subjects 15 min after using the Dan Feng peony extract facial mask was increased from 100% to 123.5%, while the average skin elasticity of the 8 subjects 15 min after using the facial mask in the control group was increased only from 100% to 108.8%. That is, the external use of the Dan Feng peony extract significantly increased the skin elasticity by 23.5%, while the facial mask in the control group increased the skin elasticity only by 8.8%.

Referring to FIG. 13, the average skin hydration of the 8 subjects 15 min after using the Dan Feng peony extract facial mask is increased from 100% to 120.2%, while the average skin hydration of the 8 subjects 15 min after using the facial mask in the control group was increased only from 100% to 113.7%. That is, the external use of the Dan Feng peony extract significantly increased the skin hydration by 20.2%, while the facial mask in the control group increased the skin elasticity only by 13.7%.

Figure 14:
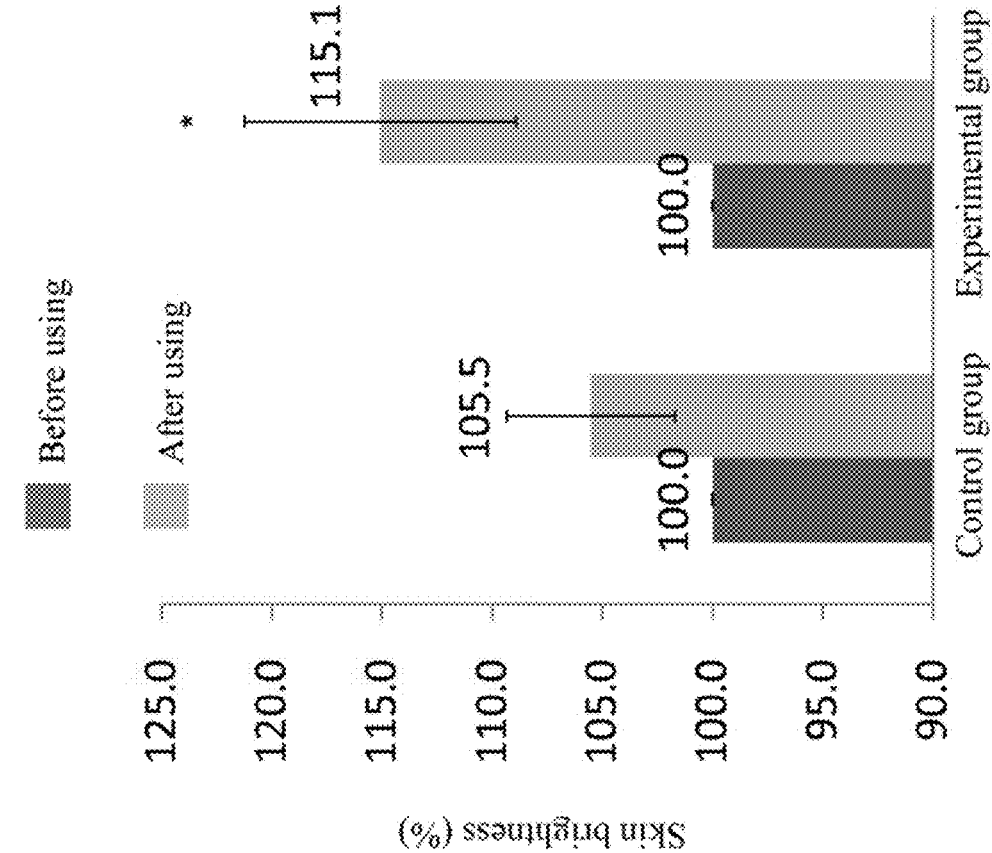
FIG. 14 is a graph showing an experimental result of the skin brightness improvement in a human subject experiment using a facial mask containing a Dan Feng peony extract.

Referring to FIG. 14, the average skin brightness of the 8 subjects 15 min after using the Dan Feng peony extract facial mask was increased from 100% to 115.1%, while the average skin brightness of the 8 subjects 15 min after using the facial mask in the control group was increased only from 100% to 105.5%. That is, the external use of the Dan Feng peony extract significantly increased the skin brightness by 15.1%, while the facial mask in the control group increased the skin elasticity only by 5.5%.

Figure 15:
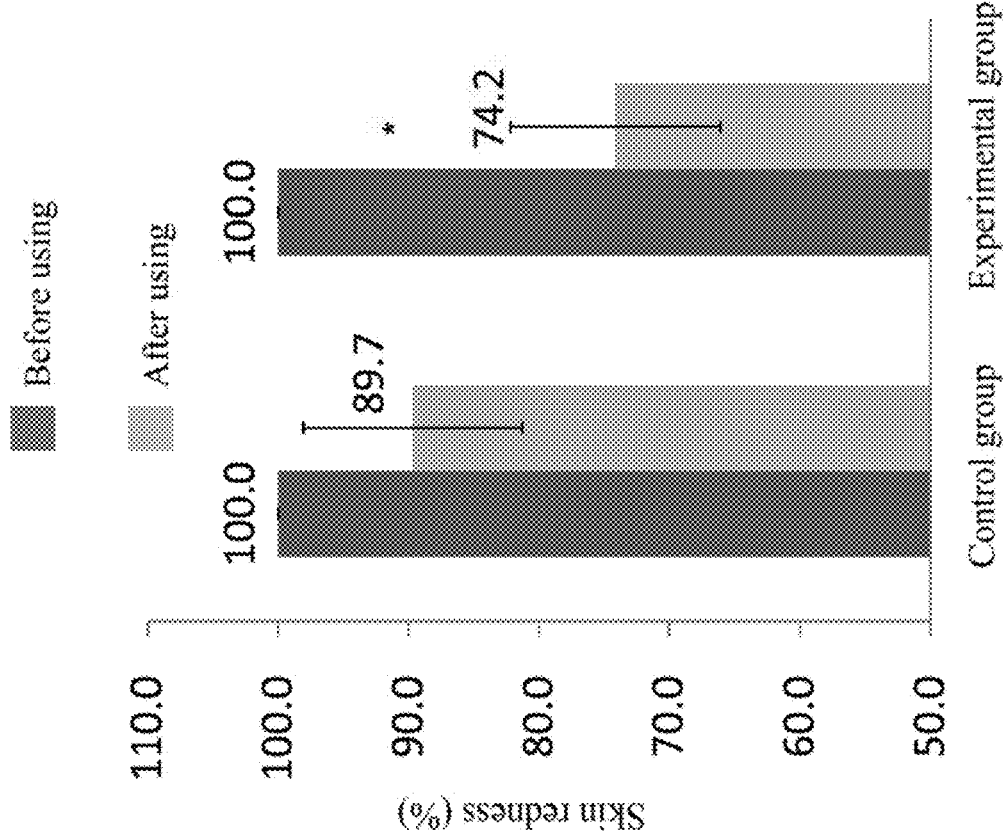
FIG. 15 is a graph showing an experimental result of the skin redness improvement in a human subject experiment using a facial mask containing a Dan Feng peony extract.

Referring to FIG. 15, the average skin redness of the 8 subjects 15 min after using the Dan Feng peony extract facial mask was reduced from 100% to 74.2%, while the average skin redness of the 8 subjects 15 min after using the facial mask in the control group was reduced from 100% to 89.7%. That is, the external use of the Dan Feng peony extract significantly reduced the skin redness by 25.8%, while the facial mask in the control group reduced the skin redness only by 10.3%.

Based on the above, the Dan Feng peony extract according to any embodiment of the present invention can be used for preparing the skin conditioning composition. In other words, the foregoing composition has one or more of the following functions: increasing the production of hyaluronic acid in skin cells, increasing the content of skin moisturizing fibers, maintaining the structure of skin keratinocytes, increasing the content of skin filaggrin, regulating the moisture content of skin cells, reducing TEWL, improving skin elasticity, and the like.

What is claimed is:

1. A method for increasing skin hydration, comprising administering to a subject with dry skin and in need of skin hydration a composition consisting of a Dan Feng peony extract, wherein the Dan Feng peony extract is extracted from flowers of Dan Feng peony, the Dan Feng peony extract is prepared by extracting the flowers of Dan Feng peony only by water, and the flowers and the water are mixed in a volume ratio of 1:15.

2. The method according to claim 1, wherein the Dan Feng peony extract increases the production of hyaluronic acid in skin cells of the subject.

3. The method according to claim 2, wherein the Dan Feng peony extract increases the expression levels of HAS2 gene and HAS3 gene in the subject.

4. The method according to claim 1, wherein the Dan Feng peony extract maintains the structure of skin keratinocytes in the subject.

5. The method according to claim 4, wherein the Dan Feng peony extract increases the expression levels of Tgm1 gene and keratin-related gene in the subject.

6. The method according to claim 1, wherein the Dan Feng peony extract regulates the moisture content of skin cells in the subject.

7. The method according to claim 6, wherein the Dan Feng peony extract increases the expression levels of AQP3 gene and GBA gene in the subject.

8. The method according to claim 1, wherein the Dan Feng peony extract increases the content of skin filaggrin in the subject.

9. The method according to claim 8, wherein the Dan Feng peony extract increases the expression level of FLG gene in the subject.

10. The method according to claim 1, wherein the Dan Feng peony extract reduces trans-epidermal water loss (TEWL) in the subject.

11. The method according to claim 1, wherein the composition is a food composition, and an effective dose of the Dan Feng peony extract in the food composition is 4 mL/day.

12. The method according to claim 1, wherein the composition is a topical composition, and an effective concentration of the Dan Feng peony extract in the topical composition is at least 5%.

* * * * *

SEQUENCE LISTING

```
<160> NUMBER OF SEQ ID NOS: 22

<210> SEQ ID NO 1
<211> LENGTH: 23
<212> TYPE: DNA
<213> ORGANISM: Artificial Sequence
<220> FEATURE:
<223> OTHER INFORMATION: HAS2-F

<400> SEQUENCE: 1
aagaacaact tccacgaaaa ggg                                           23

<210> SEQ ID NO 2
<211> LENGTH: 19
<212> TYPE: DNA
<213> ORGANISM: Artificial Sequence
<220> FEATURE:
<223> OTHER INFORMATION: HAS2-R

<400> SEQUENCE: 2
cgcagcaact tccatgagg                                                19

<210> SEQ ID NO 3
<211> LENGTH: 23
<212> TYPE: DNA
<213> ORGANISM: Artificial Sequence
<220> FEATURE:
<223> OTHER INFORMATION: HAS3-F

<400> SEQUENCE: 3
aagaacaact tccacgaaaa ggg                                           23

<210> SEQ ID NO 4
<211> LENGTH: 19
<212> TYPE: DNA
<213> ORGANISM: Artificial Sequence
<220> FEATURE:
<223> OTHER INFORMATION: HAS3-R

<400> SEQUENCE: 4
cgcagcaact tccatgagg                                                19

<210> SEQ ID NO 5
<211> LENGTH: 19
<212> TYPE: DNA
<213> ORGANISM: Artificial Sequence
<220> FEATURE:
<223> OTHER INFORMATION: GAPDH-F

<400> SEQUENCE: 5
ctgggctaca ctgagcacc                                                19

<210> SEQ ID NO 6
<211> LENGTH: 21
<212> TYPE: DNA
<213> ORGANISM: Artificial Sequence
<220> FEATURE:
<223> OTHER INFORMATION: GAPDH-R
```

```
<400> SEQUENCE: 6
aagtggtcgt tgagggcaat g                                              21

<210> SEQ ID NO 7
<211> LENGTH: 22
<212> TYPE: DNA
<213> ORGANISM: Artificial Sequence
<220> FEATURE:
<223> OTHER INFORMATION: TGM1-F

<400> SEQUENCE: 7
gatcgcatca cccttgagtt ac                                             22

<210> SEQ ID NO 8
<211> LENGTH: 19
<212> TYPE: DNA
<213> ORGANISM: Artificial Sequence
<220> FEATURE:
<223> OTHER INFORMATION: TGM1-R

<400> SEQUENCE: 8
gcaggttcag attctgccc                                                 19

<210> SEQ ID NO 9
<211> LENGTH: 21
<212> TYPE: DNA
<213> ORGANISM: Artificial Sequence
<220> FEATURE:
<223> OTHER INFORMATION: KRT1-F

<400> SEQUENCE: 9
agagtggacc aactgaagag t                                              21

<210> SEQ ID NO 10
<211> LENGTH: 21
<212> TYPE: DNA
<213> ORGANISM: Artificial Sequence
<220> FEATURE:
<223> OTHER INFORMATION: KRT1-R

<400> SEQUENCE: 10
attctctgca tttgtccgct t                                              21

<210> SEQ ID NO 11
<211> LENGTH: 22
<212> TYPE: DNA
<213> ORGANISM: Artificial Sequence
<220> FEATURE:
<223> OTHER INFORMATION: KRT10-F

<400> SEQUENCE: 11
tcctacttgg acaaagttcg gg                                             22

<210> SEQ ID NO 12
<211> LENGTH: 19
<212> TYPE: DNA
<213> ORGANISM: Artificial Sequence
<220> FEATURE:
<223> OTHER INFORMATION: KRT10-R

<400> SEQUENCE: 12
cccctgatgt gagttgcca                                                 19

<210> SEQ ID NO 13
<211> LENGTH: 20
```

```
<212> TYPE: DNA
<213> ORGANISM: Artificial Sequence
<220> FEATURE:
<223> OTHER INFORMATION: KRT14-F

<400> SEQUENCE: 13
ttctgaacga gatgcgtgac                                        20

<210> SEQ ID NO 14
<211> LENGTH: 20
<212> TYPE: DNA
<213> ORGANISM: Artificial Sequence
<220> FEATURE:
<223> OTHER INFORMATION: KRT14-R

<400> SEQUENCE: 14
gcagctcaat ctccaggttc                                        20

<210> SEQ ID NO 15
<211> LENGTH: 20
<212> TYPE: DNA
<213> ORGANISM: Artificial Sequence
<220> FEATURE:
<223> OTHER INFORMATION: TBP-F

<400> SEQUENCE: 15
tataatccca agcggtttgc                                        20

<210> SEQ ID NO 16
<211> LENGTH: 20
<212> TYPE: DNA
<213> ORGANISM: Artificial Sequence
<220> FEATURE:
<223> OTHER INFORMATION: TBP-R

<400> SEQUENCE: 16
gctggaaaac ccaacttctg                                        20

<210> SEQ ID NO 17
<211> LENGTH: 20
<212> TYPE: DNA
<213> ORGANISM: Artificial Sequence
<220> FEATURE:
<223> OTHER INFORMATION: FLG-F

<400> SEQUENCE: 17
ggcaaatcct gaagaatcca                                        20

<210> SEQ ID NO 18
<211> LENGTH: 20
<212> TYPE: DNA
<213> ORGANISM: Artificial Sequence
<220> FEATURE:
<223> OTHER INFORMATION: FLG-R

<400> SEQUENCE: 18
gctggaaaac ccaacttctg                                        20

<210> SEQ ID NO 19
<211> LENGTH: 19
<212> TYPE: DNA
<213> ORGANISM: Artificial Sequence
<220> FEATURE:
<223> OTHER INFORMATION: AQP3-F

<400> SEQUENCE: 19
```

```
ggggagatgc tccacatcc                                                  19

<210> SEQ ID NO 20
<211> LENGTH: 21
<212> TYPE: DNA
<213> ORGANISM: Artificial Sequence
<220> FEATURE:
<223> OTHER INFORMATION: AQP3-R

<400> SEQUENCE: 20
aaaggccagg ttgatggtga g                                               21

<210> SEQ ID NO 21
<211> LENGTH: 20
<212> TYPE: DNA
<213> ORGANISM: Artificial Sequence
<220> FEATURE:
<223> OTHER INFORMATION: GBA -F

<400> SEQUENCE: 21
tccagttgca caacttcagc                                                 20

<210> SEQ ID NO 22
<211> LENGTH: 20
<212> TYPE: DNA
<213> ORGANISM: Artificial Sequence
<220> FEATURE:
<223> OTHER INFORMATION: GBA -R

<400> SEQUENCE: 22
ttgtgctcag cataggcatc                                                 20
```